United States Patent [19]

Kühle et al.

[11] Patent Number: 4,482,737

[45] Date of Patent: Nov. 13, 1984

[54] PREPARATION OF N-SUBSTITUTED N-ISOCYANATOCARBONYL-CARBAMATES

[75] Inventors: Engelbert Kühle, Bergisch-Gladbach; Hermann Hagemann, Leverkusen, both of Fed. Rep. of Germany

[73] Assignee: Bayer Aktiengesellschaft, Leverkusen, Fed. Rep. of Germany

[21] Appl. No.: 439,101

[22] Filed: Nov. 3, 1982

[30] Foreign Application Priority Data

Nov. 21, 1981 [DE] Fed. Rep. of Germany ....... 3146230

[51] Int. Cl.$^3$ ................ C07C 125/065; C07C 125/067
[52] U.S. Cl. ....................................... 560/115; 71/98; 260/465 D; 260/465.4; 560/18; 560/22; 560/137; 560/148; 560/156; 560/159; 549/467
[58] Field of Search ................. 560/33, 115, 137, 148, 560/159, 18, 22, 156; 260/465 D, 465.4; 549/467

[56] References Cited

U.S. PATENT DOCUMENTS 3,919,280 11/1975 Rosenthal et al. .............. 260/453 P
3,962,302 6/1976 Rosenthal et al. .............. 260/453 P

OTHER PUBLICATIONS

Synthesis, 1980, p. 112, V. I. Gorbatenko et al., "Reactions of Chlorocarbonyl Isocyanate with Carbamates and Ureas Containing an N—H Bond".

Primary Examiner—Dolph H. Torrence
Attorney, Agent, or Firm—Sprung, Horn, Kramer & Woods

[57] ABSTRACT

N-substituted N-isocyanatocarbonyl-carbamates, some of which are new, of the general formula

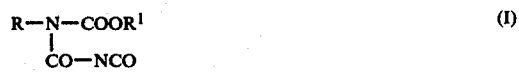

$$R-N-COOR^1 \quad\quad (I)$$
$$\;\;\;\;|$$
$$\;\;\;\;CO-NCO$$

are prepared by reacting an N-substituted carbamic acid ester of the general formula

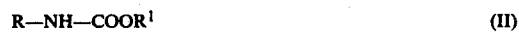

$$R-NH-COOR^1 \quad\quad (II)$$

with chlorocarbonyl isocyanate of the formula

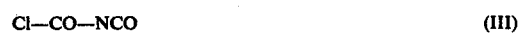

$$Cl-CO-NCO \quad\quad (III)$$

in a diluent, at a temperature between 50° and 200° C. The compounds (I) can be used as intermediate products for the preparation of new pest-combating agents.

11 Claims, No Drawings

PREPARATION OF N-SUBSTITUTED N-ISOCYANATOCARBONYL-CARBAMATES

The present invention relates to an unobvious process for the production of N-substituted N-isocyanatocarbonyl-carbamates, which can be used, for example, as intermediate products for the preparation of pest combating agents, and of which the majority are new.

It has already been disclosed that N-substituted O-alkyl N-isocyanatocarbonyl-carbamates are obtained when corresponding N-substituted O-alkyl carbamates are reacted with chlorocarbonyl isocyanate in the presence of a tertiary amine as an acid-binding agent, if appropriate in the presence of a solvent (see Synthesis 1980, 112).

However, this process has the disadvantage that a salt is formed as a by-product in the reaction and adversely affects the cost-efficiency of the process.

The present invention now provides a process for the production of an N-substituted N-isocyanatocarbonyl-carbamate of the general formula

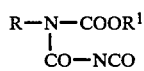
(I)

in which R and $R^1$ are identical or different and individually represent an optionally substituted radical of the aliphatic, cycloaliphatic, araliphatic or aromatic series, which is characterized in that an N-substituted carbamic acid ester of the general formula

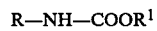
(II)

in which R and $R^1$ have the meanings given above, is reacted with chlorocarbonyl isocyanate of the formula

(III)

at a temperature between 50° and 200° C., in a diluent.

The present invention further provides, as new compounds, the N-substituted N-isocyanatocarbonyl-carbamates of the general formula

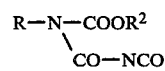
(Ia)

in which
R represents an optionally substituted radical of the aliphatic, cycloaliphatic, araliphatic or aromatic series, and
$R^2$ represents an optionally substituted radical of the cycloaliphatic, araliphatic or aromatic series.

The new N-substituted N-isocyanatocarbonyl-carbamates of the formula (Ia) can be obtained by a particular form of the process of the invention in which an N-substituted carbamic acid ester of the general formula

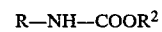
(IIa)

in which R and $R^2$ have the meaning given above, is reacted with chlorocarbonyl isocyanate of the formula

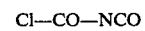
(III)

at a temperature between 50° and 200° C., in a diluent.

It is particularly surprising that the reaction according to the invention proceeds so smoothly and without the formation of by-products, at an elevated temperature. It was rather to be expected that, before the reaction with the chlorocarbonyl isocyanate of the formula (III), the N-substituted carbamic acid esters of the formula (II) or (IIa) to be employed as starting materials would be split, at the elevated temperature, to form isocyanates and alcohols or phenols, which in turn could then react with the chlorocarbonyl isocyanate of the formula (III).

Furthermore, it should be emphasized that, compared to the known process, the process according to the invention has the advantage that gaseous hydrogen chloride is formed as the by-product and escapes or can be led away continuously from the reaction system. Thus, it is possible to dispense with the procedures of separating off and working up the salt obtained in the known process, which procedures could have led to difficulties in view of the fact that the reaction products are very sensitive to hydrolysis. The N-substituted N-isocyanatocarbonyl-carbamates are obtained in very good yields and high purity by the process according to the invention.

If, for example, O-phenyl N-methylcarbamate and chlorocarbonyl isocyanate are used as starting materials, the course of the reaction according to the present invention is illustrated by the following equation:

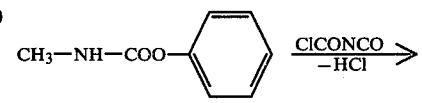

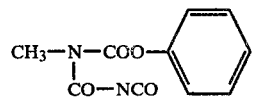

N-substituted carbamic acid esters of formula (II) or (IIa) to be used as starting materials in the process according to the invention comprise radicals having the following meanings:

In these formulae, the optionally substituted radical of the aliphatic series R and $R^1$ is generally optionally substituted alkyl, alkenyl or alkinyl.

The optionally substituted radical of the cycloaliphatic series R, $R^1$ and $R^2$ is generally an optionally substituted cycloalkyl radical or an optionally substituted cycloalkenyl radical.

The optionally substituted radical of the araliphatic series R, $R^1$ and $R^2$ is generally an optionally substituted aralkyl radical or an optionally substituted aralkenyl radical.

The optionally substituted radical of the aromatic series R, $R^1$ and $R^2$ is generally an optionally substituted aryl radical.

Optionally substituted alkyl R and $R^1$ is preferably straight-chain or branched alkyl having 1 to 20, more preferably 1 to 10, especially 1 to 5, carbon atoms. Optionally substituted methyl, ethyl, n- and i-propyl, n-, i-, sec- and tert.-butyl may be mentioned as examples.

Optionally substituted alkenyl R and $R^1$ is preferably straight-chain or branched alkenyl having 2 to 10, more preferably 2 and 8, especially 2 to 4, carbon atoms. Optionally substituted ethenyl, propen-1-yl, propen-2-yl and butenyl may be mentioned as examples.

Optionally substituted alkinyl R and $R^1$ is preferably straight-chain or branched alkinyl having 2 to 10, more preferably 2 to 8, in particular 2 to 4, carbon atoms.

Optionally substituted ethinyl, propin-1-yl, propin-3-yl and butinyl may be mentioned as examples.

The optionally substituted cycloalkyl radical R, $R^1$ and $R^2$ is preferably a monocyclic and bicyclic cycloalkyl having 3 to 8, more preferably 5 to 8, especially 5 or 6, carbon atoms. Optionally substituted cyclopentyl or cyclohexyl may be mentioned as examples.

The optionally substituted cycloalkenyl radical R, $R^1$ and $R^2$ is preferably a monocyclic cycloalkenyl having 5 or 6 carbon atoms and 1 or 2 double bonds.

The optionally substituted aralkyl radical R, $R^1$ and $R^2$ is preferably aralkyl which is optionally substituted in the aryl part and/or alkyl part and which has 6 to 10, preferably 6, carbon atoms in the aryl part and 1 to 6, more preferably 1 to 4, carbon atoms, especially 1 or 2 carbon atoms, in the alkyl part, it being possible for the alkyl part to be straight-chain or branched. Optionally sustituted benzyl and phenylethyl may be mentioned as examples.

Optionally substituted aralkenyl R, $R^1$ and $R^2$ preferably corresponds in its aryl part to the preferred aralkyl radical in R, $R^1$ and $R^2$. It conatins in the alkenyl part preferably 2 to 6, especially 2 or 3, carbon atoms, and preferably 1 double bond.

Optionally substituted aryl R, $R^1$ and $R^2$ is preferably aryl having 6 to 10 carbon atoms in the aryl part. Optionally substituted phenyl or naphthyl, in particular phenyl, may be mentioned as examples.

The substituted radicals mentioned in the definitions of R, $R^1$ and $R^2$ can carry one or more identical or different substituents.

The following may be listed as examples of substituents of the substituted alkyl radicals, substituted alkenyl radicals and substituted alkinyl radicals defined in R and $R^1$: alkoxy having preferably 1 to 4, especially 1 or 2, carbon atoms, such as methoxy, ethoxy, n- or i-propoxy and n-, i-, sec.- and tert.-butoxy, alkylthio having preferably 1 to 4, especially 1 or 2, carbon atoms, such as methylthio, ethylthio, n- and isopropylthio and n-, i-, sec.- and tert.-butylthio; halogen, preferably fluorine, chlorine, bromine and iodine, especially chlorine and bromine; cyano and nitro.

The following may be listed as examples of substituents of the substituted cycloalkyl or substituted cycloalkenyl defined in R, $R^1$ and $R^2$: alkyl having 1 to 4, especially 1 or 2, carbon atoms, such as methyl, ethyl, n- and i-propyl, n-, i-, sec.- and tert.-butyl.

The following may be listed as examples of substituents of the aryl part of the substituted aralkyl defined in R, $R^1$ and $R^2$: alkyl having 1 to 4, especially 1 or 2, carbon atoms; alkoxy having 1 to 4, especially 1 or 2, carbon atoms; halogen, preferably fluorine, chlorine, bromine and iodine, especially fluorine or chlorine; nitro; cyano and trifluoromethyl.

The following may be mentioned as examples of substituents of the aryl radical defined in R, $R^1$ and $R^2$: alkyl having 1 to 4, especially 1 or 2, carbon atoms, alkoxy having 1 to 4, especially 1 or 2, carbon atoms, halogen, preferably fluorine, chlorine, bromine and iodine, especially fluorine or chlorine; cyano; nitro; trifluoromethyl or a fused heterocyclic ring. Other non-interfering substituents may also be present.

The present invention thus provides, as preferred compounds of formula (Ia) those, in which R represents an optionally substituted alkyl, alkenyl, alkinyl, cycloalkyl, cycloalkenyl, aralkyl, aralkenyl or aryl radical, and $R^2$ represents an optionally substituted cycloalkyl, cycloalkenyl, aralkyl, aralkenyl or aryl radical.

Particularly preferred compounds of formula (Ia) are those in which

R represents an optionally substituted $C_1$ to $C_{20}$ alkyl, $C_2$ to $C_{10}$ alkenyl or $C_2$ to $C_{10}$ alkinyl radical, an optionally substituted $C_3$ to $C_8$ monocyclic cycloalkyl or $C_5$ or $C_6$ cycloalkenyl radical, an optionally substituted aralkyl radical having 6 to 10 carbon atoms in the aryl part and 1 to 4 carbon atoms in the alkyl part, an optionally substituted aralkenyl radical having 6 to 10 carbon atoms in the aryl part and 2 to 6 carbon atoms in the alkenyl part, or an optionally substituted $C_6$ to $C_{10}$ aryl radical, and $R^2$ represents an optionally substituted $C_3$ to $C_8$ monocyclic cycloalkyl or $C_5$ or $C_6$ cycloalkenyl radical, an optionally substituted aralkyl radical having 6 to 10 carbon atoms in the aryl part and 1 to 4 carbon atoms in the alkyl part, an optionally substituted aralkenyl radical having 6 to 10 carbon atoms in the aryl part and 2 to 6 carbon atoms in te alkenyl part, or an optionally substituted $C_6$ to $C_{10}$ aryl radical.

Especially preferred compounds of the formula (Ia) are those in which

R and $R^2$ represent a cyclohexyl radical which is optionally substituted by methyl or ethyl, a phenyl radical which is optionally substituted by fluorine, chlorine, nitro, methyl, ethyl, methoxy, ethoxy, n- and i-propoxy, nitro, cyano, trifluoromethyl or dimethyldihydrofuranyl, a naphthyl radical which is optionally substituted by fluroine, chlorine, methyl, ethyl, methoxy, ethoxy, n- and i-propoxy, nitro or trifluoromethyl, or a phenylethyl or phenylmethyl radical which is optionally substituted in the phenyl part by methyl, ethyl, methoxy, ethoxy, fluorine, chlorine, nitro, cyano or trifluoromethyl, and R additionally can represent an alkyl radical which has 1 to 6 carbon atoms and is optionally substituted by fluorine, chlorine, methoxy, ethoxy, methylthio, ethylthio, cyano or nitro, or represents a $C_2$ to $C_5$ alkenyl radical.

Starting compounds of the formula (II) or (IIa) are known and can be prepared according to known processes, for example by the addition of alcohols or phenols to isocyanates (see Houben-Weyl: Methoden der Organ. Chemie [Methods of Organic Chemistry], 4th Edition, Volume 8, page 141 (1952)), or by the reaction of carbonic acid ester-chlorides with primary amines (see loc. cit. page 138).

The chlorocarbonyl isocyanate further to be used as a starting material is known (see Angew. Chemie 89, 789 (1977)).

The process according to the invention is preferably carried out in the presence of a diluent. Suitable diluents are any of the inert solvents, such as hydrocarbons (for example toluene or xylene), chlorinated hydrocarbons (for example chlorobenzene) or ethers (for example dioxane).

The process according to the invention is carried out without the addition of an acid-binding agent. Advantageously, the chlorocarbonyl isocyanate is initially introduced as a solution, and should be present in the reaction medium in excess. The molar ratio of chlorocarbonyl isocyanate to carbamic acid ester can generally vary within a range from 1:1 to 10:1, preferably from 1.1:1 to 2:1.

The reaction temperatures can be varied within the relatively wide range between 50° and 200° C., preferably between 100° and 150° C.

The process according to the invention is preferably carried out under normal pressure.

In a preferred embodiment of the process according to the invention, the N-substituted carbamic acid ester of the formula (II) or (IIa) is dissolved in one of the diluents given above, and the solution is added dropwise to the chlorocarbonyl isocyanate of the formula (III), which is dissolved in one of the diluents given above. The reaction solution is heated, hydrogen chloride escaping as a gas at 95° C. and above. After the reaction mixture has been heated for several hours, it is worked up by distilling off the solvent. The isolation of the compounds is effected in a simple manner by distillation.

On standing for a relatively long time, the compounds according to the invention dimerize very readily, and this can be detected by crystallization or viscosity. By thermal treatment, for example by redistillation, the dimers are readily cleaved to give the monomeric compounds once again.

The new compounds according to the invention, of the formula (Ia), can be used as intermediate products for the preparation of new N-sulphenylated biuret N''-carboxylic acid esters. For the preparation, an N-substituted N-isocyanatocarbonyl-carbamate of the formula (Ia), of the present invention, is reacted with a sulphenamide of the general formula

(IV)

in which
R³ represents a hydrogen atom or an optionally substituted aliphatic, cycloaliphatic, araliphatic or aromatic radical, and
R⁴ represents a trihalogenomethyl radical,
in the presence of a diluent at a temperature between 0° and 150° C., preferably between 20° and 120° C. The reaction mixture is worked up by distilling off the diluent. The end products are obtained in either an oily or a crystalline form. These compounds can be used as plant protection agents. They possess, inter alia, a very good fungicidal action.

The N-sulphenylated biuret N''-carboxylic and ester active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minearls, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesvies such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestufs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g are generally required.

For the treatment of soil, active compound concentrations of 0.00001 to 0.1% by weight, preferably 0.0001 to 0.02%, are generally required at the place of action.

The process according to the invention is illustrated by the preparative examples which follow:

Preparative Example

EXAMPLE 1

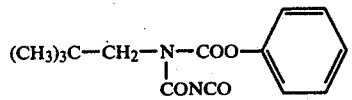   (1)

62 g (0.3 mol) of O-phenyl N-neopentylcarbamate were dissolved in 200 ml of dry chlorobenzene, and the solution was added dropwise to a solution of 35 g (0.33 mol) of chlorocarbonyl isocyanate in 70 ml of dry chlorobenzene. No noticeable reaction occurred at room temperature. When the reaction solution was heated, hydrogen chloride was evolved continuously at 95° and above. After about 1.5 to 2 hours, when the boiling point of the chlorobenzene was reached, this evolution of gas ceased. The solvent was distilled off in vacuo. By distillation under a high vacuum, the residue gave 68 g of O-phenyl N-neopentyl-N-isocyanato-carbonyl-carbamate of boiling point 111° to 112° C./0.1 mm Hg (88% of theory).

The following compounds of the formula (I) were obtained in an analogous manner $$\begin{array}{c} R-N-COOR^1 \\ | \\ CO-NCO \end{array} \quad (I)$$

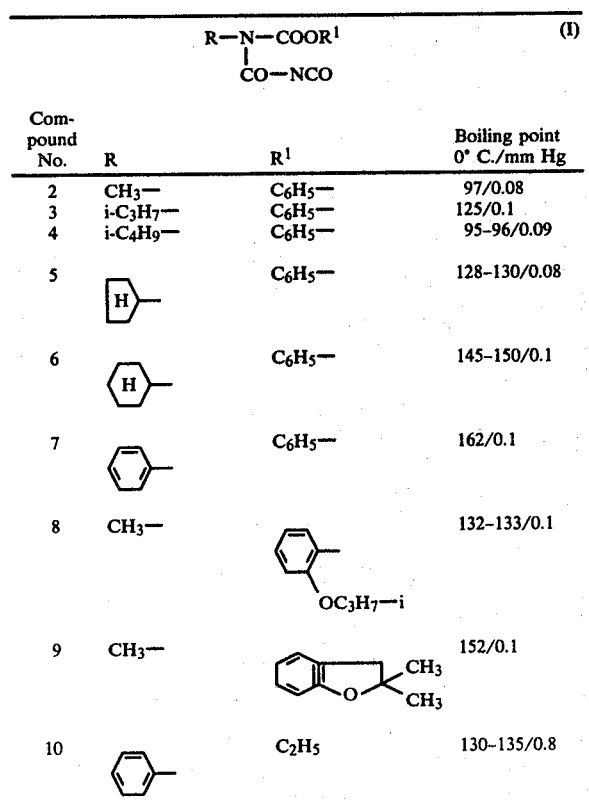

| Compound No. | R | $R^1$ | Boiling point 0° C./mm Hg |
|---|---|---|---|
| 2 | $CH_3-$ | $C_6H_5-$ | 97/0.08 |
| 3 | $i-C_3H_7-$ | $C_6H_5-$ | 125/0.1 |
| 4 | $i-C_4H_9-$ | $C_6H_5-$ | 95-96/0.09 |
| 5 | [H-phenyl] | $C_6H_5-$ | 128-130/0.08 |
| 6 | [H-phenyl] | $C_6H_5-$ | 145-150/0.1 |
| 7 | [phenyl] | $C_6H_5-$ | 162/0.1 |
| 8 | $CH_3-$ | [o-i-propoxyphenyl] | 132-133/0.1 |
| 9 | $CH_3-$ | [2,2-dimethylbenzodioxolyl] | 152/0.1 |
| 10 | [phenyl] | $C_2H_5$ | 130-135/0.8 |

$$\begin{array}{c} R-N-COOR^1 \\ | \\ CO-NCO \end{array} \quad (I)$$

| Compound No. | R | $R^1$ | Boiling point 0° C./mm Hg |
|---|---|---|---|
| 11 | $(CH_3)_3C-CH_2-$ | $C_2H_5$ | 70-74/0.2 |

Preparation of an N-sulphenylated biuret-N'''-carboxylic acid ester

EXAMPLE 2

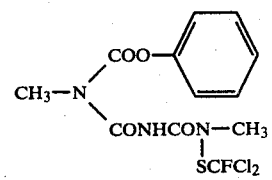

14 g (0.063 mol) of O-phenyl N-methyl-N-(isocyanatocarbonyl)-carbamate were dissolved in 50 ml of dioxane, and 10.5 g (0.07 mol) of fluorodichloromethanesulphenyl-N-methylamide were added dropwise to the solution at room temperature. The temperature increased to 60° C. during this process. The reaction solution was concentrated in vacuo, and the residue was recrystallized from methanol. M.P.: 119° to 120° C., yield 18 g (78% of theory).

The fungicidal activity of the active compounds produced from the compounds of this invention is illustrated by the following biotest example:

EXAMPLE 3

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound was mixed with the stated amount of solvent, and the concentrate was diluted with water and the stated amount of emulsifier, to the desired concentration.

To test for protective activity, young rice plants were sprayed with the preparation of active compound until dripping wet. After the spray coating had dried off, the plants were inoculated with an aqueous spore suspension of *Pyricularia oryzae*. The plants were then placed in a greenhouse at 100% relative atmospheric humidity and 25° C.

Evaluation of the disease infestation was carried out 4 days after the inoculation.

In this test, a clearly superior activity compared with the prior art was shown by the compound of Example 2.

It is understood that the specification and examples are illustrative but not limitative of the present invention and that other embodiments within the spirit and scope of the invention will suggest themselves to those skilled in the art.

We claim:
1. A process for the production of an N-substituted N-isocyanatocarbonyl-carbamate of the formula

```
R—N—COOR¹
    |
   CO—NCO
``` in which R and R¹ each independently is an alkyl radical having 1 to 20 carbon atoms, or an alkenyl or alkinyl radical having 2 to 10 carbon atoms, each optionally substituted by alkoxy or alkylthio having 1 to 4 carbon atoms, halogen, cyano and/or nitro; a cycloalkyl radical having 3 to 8 carbon atoms, or a cycloalkenyl radical having 5 or 6 carbon atoms and 1 or 2 double bonds, each optionally substituted by alkyl having 1 to 4 carbon atoms; an aryl radical having 6 to 10 carbon atoms in the aryl part and 1 to 6 carbon atoms in the alkyl part, and optionally substituted by alkyl or alkoxy having 1 to 4 carbon atoms, halogen, nitro, cyano and/or trifluoromethyl; an aralkenyl radical having 6 to 10 carbon atoms in the aryl part and 1 to 6 carbon atoms in the alkenyl part; or an aryl radical having 6 to 10 carbon atoms and optionally substituted by alkyl or alkoxy having 1 to 4 carbon atoms, halogen, cyano, nitro, trifluoromethyl and/or a fused heterocyclic ring, comprising reacting an N-substituted carbamic acid ester of the formula

```
R—NH—COOR¹
``` with chlorocarbonyl isocyanate of the formula

```
Cl—CO—NCO
``` at a temperature between about 50° and 200° C. in a diluent.

2. A process according to claim 1, wherein the reaction is carried out at a temperature between about 100° and 150° C.

3. A process according to claim 1, wherein the diluent is a hydrocarbon, a chlorinated hydrocarbon or an ether.

4. A process according to claim 1, wherein the molar ratio of the chlorocarbonyl isocyanate to the N-substituted carbamic acid ester is from about 1:1 to 10:1.

5. A process according to claim 3, wherein the reaction is carried out at a temperature between about 100° and 150° C. and the molar ratio of the chlorocarbonyl isocyanate to the N-substituted carbamic acid ester is from about 1.1:1 to 2:1.

6. An N-substituted N-isocyanatocarbonylcarbamate of the formula

```
R—N—COOR²
    |
   CO—NCO
``` in which
R is an optionally substituted C₁ to C₂₀ alkyl, C₂ to C₁₀ alkenyl or C₂ to C₁₀ alkinyl radical an optionally substituted C₃ to C₈ monocyclic cycloalkyl or C₅ or C₆ cycloalkenyl radical, an optionally substituted aralkyl radical having 6 to 10 carbon atoms in the aryl part and 1 to 4 carbon atoms in the alkyl part, an optionally substituted aralkenyl radical having 6 to 10 carbon atoms in the aryl part and 2 to 6 carbon atoms in the alkenyl part, or an optionally substituted C₆ to C₁₀ aryl radical, and R² is an optionally substituted C₃ to C₈ monocyclic cycloalkyl or C₅ or C₆ cycloalkenyl radical, an optionally substituted aralkyl radical having 6 to 10 carbon atoms in the aryl part and 1 to 4 carbon atoms in the alkyl part, an optionally substituted aralkenyl radical having 6 to 10 carbon atoms in the aryl part and 2 to 6 carbon atoms in the alkenyl part, or an optionally substituted C₆ to C₁₀ aryl radical.

7. A compound according to claim 6, wherein such compound is O-phenyl N-neopentyl-N-isocyanato-carbonylcarbonyl-carbamate of the formula

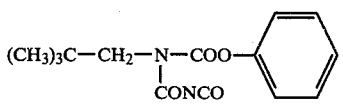

8. A compound according to claim 6, wherein such compound is O-phenyl N-methyl-N-isocyanato-carbonyl-carbamate of the formula

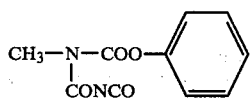

9. A compound according to claim 6, wherein such compound is O-phenyl N-isopropyl-N-isocyanato-carbonyl-carbamate of the formula

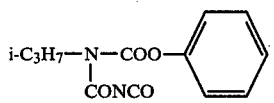

10. A compound according to claim 6, wherein such compound is O-phenyl N-isobutyl-N-isocyanato-carbonyl-carbamate of the formula

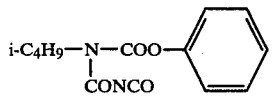

11. A compound according to claim 6, wherein such compound is O-phenyl N-cyclopentyl-N-isocyanato-carbonylcarbamate of the formula

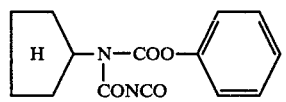

* * * * *